(12) United States Patent
Fecher et al.

(10) Patent No.: US 11,370,702 B2
(45) Date of Patent: Jun. 28, 2022

(54) METHOD TO INCREASE THE STRENGTH OF A FORM BODY OF A LITHIUM SILICATE GLASS CERAMIC

(71) Applicant: DENTSPLY SIRONA Inc., York, PA (US)

(72) Inventors: Stefan Fecher, Johannesberg (DE); Lothar Völkl, Goldbach (DE)

(73) Assignee: DENTSPLY SIRONA INC., York, PA (US)

(*) Notice: Subject to any disclaimer, the term of this patent is extended or adjusted under 35 U.S.C. 154(b) by 258 days.

(21) Appl. No.: 15/160,432

(22) Filed: May 20, 2016

(65) Prior Publication Data
US 2016/0340237 A1 Nov. 24, 2016

(51) Int. Cl.
| | |
|---|---|
| *C03B 32/00* | (2006.01) |
| *C03C 21/00* | (2006.01) |
| *C03C 4/00* | (2006.01) |
| *C03C 3/097* | (2006.01) |
| *A61K 6/804* | (2020.01) |
| *A61K 6/818* | (2020.01) |
| *A61K 6/822* | (2020.01) |
| *A61K 6/824* | (2020.01) |
| *A61K 6/833* | (2020.01) |
| *A61K 6/853* | (2020.01) |

(Continued)

(52) U.S. Cl.
CPC ............ *C03C 21/002* (2013.01); *A61K 6/804* (2020.01); *A61K 6/818* (2020.01); *A61K 6/822* (2020.01); *A61K 6/824* (2020.01); *A61K 6/833* (2020.01); *A61K 6/853* (2020.01); *C03B 25/00* (2013.01); *C03C 3/097* (2013.01); *C03C 4/0021* (2013.01); *C03C 10/0027* (2013.01); *C03C 2204/00* (2013.01)

(58) Field of Classification Search
CPC ................................ C03B 32/00; C03C 21/00
See application file for complete search history.

(56) References Cited

U.S. PATENT DOCUMENTS

| | | | | |
|---|---|---|---|---|
| 3,912,480 | A | * | 10/1975 | Boguslavsky .......... C03B 25/02 264/70 |
| 4,546,006 | A | | 10/1985 | Ohno |
| 4,784,606 | A | | 11/1988 | Jones |

(Continued)

FOREIGN PATENT DOCUMENTS

| | | |
|---|---|---|
| AU | 2016267538 B2 | 9/2020 |
| BE | 618738 A | 12/1962 |

(Continued)

OTHER PUBLICATIONS

European Search Report; EP16170624; Jul. 12, 2016 (completed).

(Continued)

*Primary Examiner* — Cynthia Szewczyk
(74) *Attorney, Agent, or Firm* — Dentsply Sirona Inc.

(57) ABSTRACT

The invention relates to a method to derive a medical form body of lithium silicate glass ceramic. To increase its strength it is proposed that in the form body comprising lithium silicate glass or containing lithium silicate glass the lithium ions are replaced by alkali ions of greater diameter to generate a surface compressive stress. To this end the form body is covered with a melt containing an alkali metal for which an aliquoted quantity of salt containing the alkali metal is used.

18 Claims, 5 Drawing Sheets

(51) Int. Cl.
*C03B 25/00* (2006.01)
*C03C 10/00* (2006.01)

(56) References Cited

U.S. PATENT DOCUMENTS

| | | | |
|---|---|---|---|
| 5,475,610 | A | 12/1995 | Atwood |
| 6,703,590 | B1 | 3/2004 | Holley |
| 2003/0099062 | A1* | 5/2003 | Kataoka ............. C03C 10/0027 360/99.12 |
| 2004/0221615 | A1* | 11/2004 | Postupack ............ C03C 21/002 65/30.14 |
| 2007/0031515 | A1* | 2/2007 | Stucky .................. A61K 33/24 424/724 |
| 2007/0039353 | A1* | 2/2007 | Kamiya ................ C03C 21/001 65/30.14 |
| 2012/0052302 | A1* | 3/2012 | Matusick ................ C03C 15/00 428/410 |
| 2012/0236526 | A1* | 9/2012 | Weber ................... C03C 21/002 361/807 |
| 2013/0295523 | A1 | 11/2013 | Durschang |
| 2014/0252272 | A1 | 9/2014 | Durschang |
| 2014/0366579 | A1* | 12/2014 | Antoine ................ C03C 21/001 65/30.14 |
| 2015/0104655 | A1 | 4/2015 | Kim |
| 2016/0039588 | A1* | 2/2016 | Sheehan ................ B65D 71/70 269/40 |
| 2016/0113845 | A1 | 4/2016 | Fecher |
| 2016/0229742 | A1 | 8/2016 | Wondraczek |
| 2016/0340237 | A1 | 11/2016 | Fecher |
| 2017/0158552 | A1 | 6/2017 | Ritzberger |

FOREIGN PATENT DOCUMENTS

| | | |
|---|---|---|
| CA | 2911284 A1 | 11/2014 |
| DE | 3015529 A1 | 11/1980 |
| DE | 19750794 A1 | 6/1999 |
| DE | 10336913 A1 | 3/2005 |
| DE | 102009060274 A1 | 6/2011 |
| DE | 202011110343 U1 | 9/2013 |
| EP | 2662342 A1 | 11/2013 |
| EP | 3053886 A1 | 8/2016 |
| EP | 3095433 A1 | 11/2016 |
| EP | 3095434 A1 | 11/2016 |
| EP | 3095435 A1 | 11/2016 |
| EP | 3095436 A1 | 11/2016 |
| FR | 2454796 A1 | 11/1980 |
| WO | 2012175450 A1 | 12/2012 |
| WO | 2013053865 A2 | 4/2013 |
| WO | 2016188904 A1 | 12/2016 |

OTHER PUBLICATIONS

International Search Report; PCT/EP2016/061439; Jul. 12, 2016 (completed); dated Jul. 20, 2016.
Observations filed by a Third Party according to Art. 115 EPC; Feb. 8, 2019; Application No. 16170624.7.
Fischer et al; "Chemical strengthening of a dental lithium disilicate glass-ceramic material"; Published Jan. 9, 2008 in Wiley InterScience; pp. 582-587.
W. Holand et al; "Glass-Ceramic Technology"; 2002; pp. 291-292.
Fischer et al.; "Improvement of Strength Parameters of a Leucite-reinforced Glass Ceramic by Dual-ion Exchange" Accepted Oct. 25, 2000; pp. 336-339.
I.L. Denry et al; "Enhanced Chemical Strengthening of Feldspathic Dental Porcelain"; J. Dent Res; Oct. 1993; pp. 142-1433.
R.R. Seghi et al.; Effects of Ion Exchange on Hardness and Fracture Toughness of Dental Ceramics; The International Journal of Prosthodontics; vol. 5, No. 4, 1992; pp. 309-314.
International Preliminary Report on Patentability; PCT/EP2016/061439; Jul. 12, 2016 (completed); dated Jul. 20, 2016.
Written Opinion of the International Searching Authority; PCT/EP2016/061439; Jul. 12, 2016 (completed); dated Jul. 20, 2016.
Canadian Office Action dated Aug. 20, 2021.

* cited by examiner a)

Formkörper b)

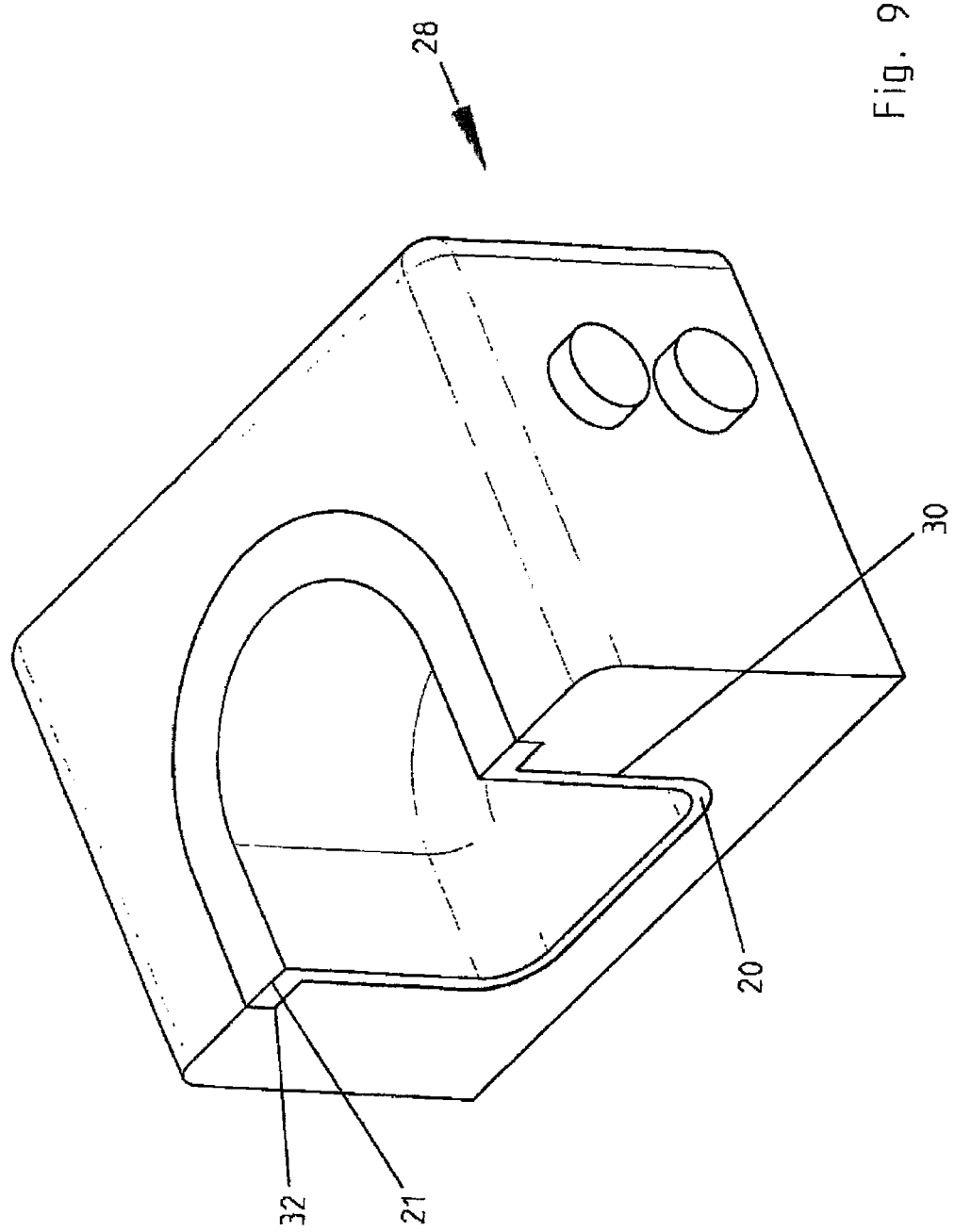

METHOD TO INCREASE THE STRENGTH OF A FORM BODY OF A LITHIUM SILICATE GLASS CERAMIC

THE CROSS-REFERENCE TO RELATED APPLICATIONS

This patent application claims the benefit of and priority to German Patent Application No. 10 2015 108 173.3, filed on May 22, 2015, which is herein incorporated by reference for all purposes.

TECHNICAL FIELD

The invention relates to a method to increase the strength of a medical form body comprising a lithium silicate glass ceramic, preferably in the form of a dental form body, or a part of such a body, in particular a bridge, crown, coping, inlay, onlay or veneer.

BACKGROUND OF THE INVENTION

A proven method in dental technology has been to use a lithium silicate glass ceramic as a blank for the fabrication of dental restorations because of its strength and biocompatibility. It has been found to be an advantage if, for a lithium silicate blank that contains lithium metasilicate as the main crystal phase, machine working is possible without difficulty, without high tool wear. Upon subsequent heat treatment, in which the product is converted into a lithium disilicate glass ceramic, it then has a high strength. It also has good optical properties and a sufficient chemical stability. Corresponding methods are disclosed in, for example, DE 197 50 794 A1 or DE 103 36 913 B4.

To achieve a high strength and at the same time a good translucency, at least one stabilizer from the group zirconium oxide, hafnium oxide or a mixture thereof, in particular zirconium oxide, is added to the raw starting materials in the form of lithium carbonate, quartz, aluminum oxide etc., i.e., the usual starting components. Attention is drawn here, for example, to DE 10 2009 060 274 A1, WO 2012/175450 A1, WO 2012/175615 A1, WO 2013/053865 A2 or EP 2 662 342 A1.

The publications of I. L. Denry et. al., Enhanced Chemical Strengthening of Feldspathic Dental Porcelain, J Dent Res, October 1993, pages 1429 to 1433, and R. R. Seghi et. al., Effects of Ion Exchange on Hardness and Fracture Toughness of Dental Ceramics, The International Journal of Prosthodontics, Volume 5, No. 4, 1992, pages 309 to 314, disclose studies of composite ceramics which are comprised of feldspathic glass types in which leucite precipitates may be present. To increase strength, it was proposed to replace sodium ions by lithium ions and then to replace lithium ions by potassium ions in a two-step process. Smaller ions can also be replaced by rubidium ions. This enabled an increase in strength of up to a maximum of 80% if rubidium oxide was used. Rubidium, however, has the disadvantage that the heat expansion coefficient of the ceramics is increased.

DE 30 15 529 A1 discloses a method to improve the mechanical strength of dental porcelain. In this method a restoration is coated with enamel so that there is an exchange of alkali ions in the enamel. For this purpose the restoration is immersed in a bath of melted salt at a temperature between 200° C. and the transition point of the enamel.

U.S. Pat. No. 4,784,606 A discloses a dental brace of glass, the strength of which is increased by ion exchange.

SUMMARY OF THE INVENTION

In one aspect, the present invention is directed to a method to increase the strength of a form body of lithium silicate glass ceramic, or a part thereof comprising the steps of: contacting at least a portion of the form body with a melt, the melt including a salt of an alkali metal or a number of alkali metals with ions of greater diameter, wherein an aliquoted quantity of salt is used for the melt; annealing the at least a portion of the form body that is in contact with the melt for a time t at a temperature T; generating a surface compressive stress in the form body of lithium silicate glass ceramic through the replacement of lithium ions by alkali metal ions of greater diameter; and removing the melt from the at least a portion of the form body.

In another aspect, the present invention is directed to a form body of lithium silicate glass ceramic comprising a surface compressive stress is generated in the form body through the replacement of lithium ions by alkali ions of greater diameter than the lithium ions.

In another aspect, the present invention is directed to a use of a capsule filled with at least one alkali metal salt to create a surface stress in a form body of a lithium silicate ceramic material through the replacement of lithium ions by alkali ions of greater diameter than the lithium ions, in that the form body is covered by the at least one alkali metal salt melted in the capsule.

In yet another aspect, it is contemplated that the of the present invention has one or any combination of the following features: further comprising the steps of: preparing a salt body from the salt as the aliquoted quantity through pressing and/or compressing; laying the salt body on the form body or laying the form body directly or indirectly on the salt body; and melting the salt body; further comprising the step of laying the form body in a first receptacle having perforations, and then immersing the first receptacle with the form body in the melt or introducing the first receptacle with the form body into the salt and the salt is then melted or laying the first receptacle with the form body on the salt or the salt body and the salt is melted at the same time as immersion of the form body in the melt that is forming; further comprising the step of enveloping the form body by a heat-resistant foil that includes the portioned quantity of salt and then melting the salt; wherein the portioned salt is made available in a second receptacle with a closure that can be removed;further comprising the step of laying the form body on the salt before melting of the salt; further comprising the step of melting the salt in the second receptacle and then immersing the form body in the melt; further comprising the step of immersing the form body with a third receptacle having perforations in the melt present in the second receptacle; further comprising the step of adding a phosphate salt to the alkali metal salt, which enables ion exchange, for the binding of lithium ions; wherein Na, K, Cs, Rb ions and any combination thereof are used as alkali metal ions to generate the surface compressive stress; wherein the melt includes one or more elements that color the form body; wherein the one or more coloring elements are one or more lanthanides with the atomic number or numbers in the range 58 to 70; wherein at least one of the one or more coloring elements is an element selected from the group consisting of vanadium, manganese, iron, yttrium, and antimony; further comprising the step of dissolving the one or more coloring elements in the melt containing alkali ions; wherein the step of annealing, the form body in is annealed in the melt, the melt including potassium ions or sodium ions, or a mixture of potassium ions and sodium ions; wherein the step of annealing, the form body is annealed at a temperature T where T≥300° C., for a time t; further comprising the step of preparing the form body from a glass melt which comprises at least the following as starting components: $SiO_2$, $Al_2O_3$, $Li_2O$, $K_2O$, at least one nucleating agent and at least one stabilizer; wherein the glass melt includes at least one coloring metal oxide; wherein the form body or a blank from which the form body is manufactured, is prepared from a glass melt that includes the following components in percentage by weight:

$SiO_2$ 50-80,
a nucleating agent 0.5-11,
$Al_2O_3$ 0-10,
$Li_2O$ 10-25,
$K_2O$ 0-13,
$Na_2O$ 0-1,
$ZrO_2$ 0-20,
$CeO_2$ 0-10,
$Tb_4O_7$ 0-8,
optionally an oxide or a number of oxides of an earth alkali metal or a number of earth alkali metals selected from the group consisting of magnesium, calcium, strontium, barium, and any combination thereof 0-20,
optionally one or more additives selected from the group consisting of $B_2O_3$, $MnO_2$, $Fe_2O_3$, $V_2O_5$, $TiO_2$, $Sb_2O_3$, ZnO, $SnO_2$, fluorides and any combination thereof 0-6,
optionally one or more oxides of the rare earth metals with the atomic numbers 57, 59-64, 66-71, 0-5; wherein the glass melt contains the following as starting components in percentage by weight
$SiO_2$ 58.1±2.0
$P_2O_5$ 5.0±1.5
$Al_2O_3$ 4.0±2.5
$Li_2O$ 16.5±4.0
$K_2O$ 2.0±0.2
$ZrO_2$ 10.0±0.5
$CeO_2$ 0-3,
$Tb_4O_7$ 0-3,
$Na_2O$ 0-0.5.

wherein the blank is formed from the glass melt in the course of cooling or following cooling to room temperature, said blank then being subject to at least one first heat treatment W1 at a temperature $T_{W1}$ for a time $t_{W1}$, wherein 620° C.≤$T_{W1}$≤800° C., and/or 1 minute≤$t_{W1}$≤200 minutes; wherein the first heat treatment W1 is carried out in two steps, wherein in a first step, a temperature $T_{St1}$ is set where 630° C.≤$T_{St1}$≤690° C. and/or in a second step a temperature $T_{St2}$ where 720° C.≤$T_{St2}$≤780° C. and/or the heating rate $A_{St1}$ up to the temperature $T_{St1}$ is 1.5 K/minute≤$A_{St1}$≤2.5 K/minute and/or the heating rate $A_{St2}$ up to the temperature $T_{St2}$ is 8 K/minute≤$T_{St2}$≤12 K/minute; wherein the lithium silicate glass ceramic blank is subjected, after the first heat treatment W1, to a second heat treatment W2 at a temperature $T_{W2}$ for a time $t_{W2}$, wherein 800° C.≤$T_{W2}$≤1040° C., and/or 2 minutes≤$t_{W2}$≤200 minutes; wherein after the first and/or second heat treatment step, the form body is prepared from the blank through grinding and/or milling or pressing, wherein the heat treatment step or steps is/are carried out during or after pressing; wherein the alkali metal ions are selected from the group consisting of Na, K, Cs, Rb ions and any combination thereof; wherein the form body or a blank from which the form body is prepared, has a glass phase which includes $ZrO_2$ that increases the strength of the form body, the concentration of which in the starting composition of the form body is 8-12% by weight; wherein the form body is prepared from a glass melt that contains the following components in percentage by weight $SiO_2$ 52-70,
$P_2O_5$ 0.5-11,
$Al_2O_3$ 0.5-5,
$Li_2O$ 13-22,
$K_2O$ 0.5-8,
$Na_2O$ 0-0.5,
$ZrO_2$ 4-16,
$CeO_2$ 0.5-8,
$Tb_4O_7$ 0.5-6,
optionally an oxide or a number of oxides of an earth alkali metal or a number of earth alkali metals selected from the group consisting of magnesium, calcium, strontium, barium, and any combination thereof 0-20,
optionally one or more additives selected from the group consisting of $B_2O_3$, $MnO_2$, $Fe_2O_3$, $V_2O_5$, $TiO_2$, $Sb_2O_3$, ZnO, $SnO_2$, fluorides and any combination thereof 0-6,
optionally one or more oxides of the rare earth metals with the atomic numbers 57, 59-64, 66-71, 0-5; wherein the form body is prepared from a glass melt that includes the following components in percentage by weight:
$SiO_2$ 58.1±2.0
$P_2O_5$ 5.0±1.5
$Al_2O_3$ 4.0±2.5
$Li_2O$ 16.5±4.0
$K_2O$ 2.0±0.2
$ZrO_2$ 10.0±0.5
$CeO_2$ 0-3,
$Tb_4O_7$ 0-3,
$Na_2O$ 0-0.5.

wherein the form body has a glass phase in the range 20-65% by volume; wherein the form body has lithium silicate crystals between 35% and 80% by volume of the body; wherein the percentage of alkali ions replacing the lithium ions, commencing from the surface down to a depth of 10 μm is in the range 5-20% by weight, and/or at a depth between 8 and 12 μm from the surface the percentage of alkali ions is in the range 5-10% by weight, and/or at a layer depth of between 12 and 14 μm from the surface the percentage of alkali ions is in the range 4-8% by weight, and/or at a depth from the surface between 14 and 18 μm the percentage of alkali ions is in the range 1-3% by weight, wherein the percentage by weight of the alkali ions diminishes from layer to layer; a heating device to melt the aliquoted salt in the second receptacle, wherein the heating device has a fifth receptacle that is at least in regions matched geometrically to the external geometry of the second receptacle; wherein the fifth receptacle is located in a heating plate of the heating device; or any combination thereof.

BRIEF DESCRIPTION OF THE DRAWINGS

Further details, advantages and characteristics of the invention derive not just from the claims, the characteristics to be derived from them—alone and/or in combination—but also from the examples given below.

FIG. 9 A heating device.

DETAILED DESCRIPTION OF THE INVENTION

Figure 1:
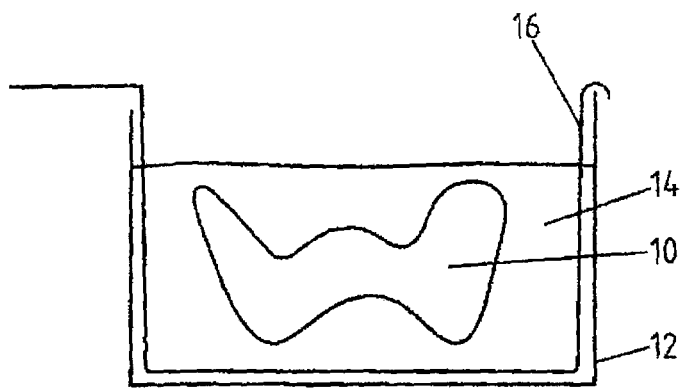
FIG. 1A schematic of a first embodiment of an arrangement to generate a surface compressive stress in a form body of a lithium silicate glass ceramic material.

The object of the present invention is to develop a method of the aforementioned type further so that using simple process technology measures the strength of the form body can be increased. With this method it should also be possible to prevent the presence of impurities in the form body through the measures necessary to increase strength.

In a further aspect, the method should also enable untrained persons to increase the strength to the desired extent.

The object of the invention is substantially achieved in that a surface compressive stress is created in the form body, comprising or containing lithium silicate glass ceramic, through replacement of lithium ions by alkali ions of greater diameter, in that the form body is covered with a melt containing corresponding alkali metal ions, and that the form body is in contact with the melt over a time t and the melt is then removed from the form body, wherein an aliquoted quantity of the salt containing the alkali metal ions is used for the melt.

It is possible to place the form body in a first receptacle such as a basket having perforations so that
- the first receptacle containing the form body is introduced into the melt or
- the salt is introduced into the first receptacle containing the form body and is melted or
- the first receptacle with the form body is placed on the salt which is then melted.

As an independently proposed solution the portioned salt is made available in a receptacle—referred to below as the second receptacle—such as a capsule, with a closure that is removable by tearing off or unscrewing. There is in particular the possibility that the form body is laid on the salt prior to the melting of the salt, or that the salt is melted in the second receptacle and the form body is then immersed in the melt. The invention also embraces the possibility that the form body with a receptacle having perforations—referred to below as the third receptacle—is immersed in the melt present in the second receptacle.

According to a further preferred proposal, the invention teaches that the body is enveloped by a heat-resistant foil as a receptacle—referred to below as the fourth receptacle—in which the portioned quantity of salt is present, and that the salt is then melted.

It was surprisingly found that when the lithium ions present in the form body of lithium silicate glass ceramic are replaced by larger alkali metal ions, a pre-stress and thus a surface compressive stress are generated, leading to a substantial increase in strength.

At the same time it was surprisingly found that the resistance to corrosion was increased. It was found that in addition to an increase in strength through ion exchange, wherein flexural strength values of above 500 MPa, preferably greater than 800 MPa, determined by the three-point bending measurement method specified in DIN EN ISO 6872-2009-01 were obtained, there was also an improvement in chemical resistance which—also determined by the method given in DIN EN ISO 6872-2009-1—yielded a chemical solubility of <95 $\mu g \times cm^{-2}$.

The alkali metal ions used to generate the surface compressive stress are preferably Na, K, Cs and/or Rb ions.

According to the invention the form body which consequently has the geometry of the body to be made available, in particular a bridge, crown, coping, inlay, onlay or veneer in the case of a dental form body, is annealed in a melt over a period of time t to enable the desired replacement of lithium ions by alkali metal ions of greater diameter with the consequence that the desired surface compressive stress is created and an increase in strength results.

It is in particular provided for the melt to be portioned in a quantity just required to fully immerse the form body, so that after annealing, i.e., after ion exchange, it is then disposed of, so that for each strength increasing process fresh salt and thus new melt is used, as a result of which compared to methods in which a melt is used more than once there is no contamination.

However, there is no departure from the invention if a corresponding melt is used more than once, even though this is not preferred.

It is in particular provided for the form body to be annealed in a melt containing potassium ions, wherein the preferred salt melt is a $KNO_3$, KCl or $K_2CO_3$ salt melt.

The invention is preferably characterized in that the form body is placed in or covered with a melt containing potassium ions, in particular a melt containing $KNO_3$, KCl or $K_2CO_3$, or a melt containing sodium ions, in particular a melt containing $NaNO_3$, sodium acetate or sodium salts of organic acids, or in a melt containing a mixture of potassium ions and sodium ions, in particular in a ratio of 50:50 mol. %, preferably in a melt containing $NaNO_3$ and $KNO_3$.

To ensure that there is a constant ion exchange potential during ion exchange, this invention further proposes that lithium ions entering the salt are bound. In particular it is proposed to bind lithium ions by adding a salt such as an alkali metal phosphate salt, like $K_2HPO_4$, to the alkali metal salt enabling ion exchange. The lithium ion content in the melt is reduced by precipitation of lithium phosphate.

Independently thereof, the required ion exchange in the surface region is found to be especially good if the form body is annealed in the melt at a temperature $T \geq 300°$ C., in particular $350°$ C.$\leq T \leq 600°$ C., preferred $430°$ C.$\leq T \leq 530°$ C., for a period of time $t \geq 5$ minutes, in particular 0.5 hours$\leq t \leq 10$ hours, especially preferred 3 hours$\leq t \leq 8$ hours.

Shorter annealing/contact times in the region of up to 30 minutes are in principle sufficient to create the desired surface compressive stress in the surface region. Insofar as an increase in strength of the form body down to a depth of 20 µm or more is desired, then longer contact/annealing times of, for example, 6 or 10 hours will be necessary, depending on the annealing temperature.

To enable the salt to be melted in an energy-conserving and temperature-controlled manner and to anneal the form body for the desired length of time the invention is characterized by a heating device with a receptacle—referred to below as the fifth receptacle—which is matched geometrically to the external dimensions of the second receptacle at least over some of its regions. It is possible for the fifth receptacle to be housed in a heating plate of the heating device.

It is preferred for the form body or a blank, from which the form body is obtained, to be fabricated from a glass melt, which contains as the starting components at least: $SiO_2$, $Al_2O_3$, $Li_2O$, $K_2O$, at least one nucleating agent, such as $P_2O_5$, and at least one stabilizer such as $ZrO_2$.

The invention is characterized in a particular manner in that not only are lithium ions replaced by larger alkali ions, in particular through potassium and/or sodium ions, but also that to increase strength in the starting substance and thus in the glass phase of the form body/blank from which the form body is derived, at least one dissolved stabilizer, in particular in the form of $ZrO_2$, is contained, wherein the concentration is preferably in the range of 8 to 12% by weight with reference to the initial composition.

In particular the invention is characterized in that the form body/blank is fabricated from a glass melt that contains the following components in percentage by weight:

$SiO_2$ 50-80, preferably 52-70, especially preferred 56-61
nucleating agent, such as P2O5, 0.5-11, preferably 3-8, especially preferred 4-7
$Al_2O_3$ 0-10, preferably 0.5-5, especially preferred 1.5-3.2
$Li_2O$ 10-25, preferably 13-22, especially preferred 14-21
$K_2O$ 0-13, preferably 0.5-8, especially preferred 1.0-2.5
$Na_2O$ 0-1, preferably 0-0.5, especially preferred 0.2-0.5
$ZrO_2$ 0-20, preferably 4-16, in particular 6-14, especially preferred 8-12
$CeO_2$ 0-10, preferably 0.5-8, especially preferred 1.0-2.5
$Tb_4O_7$ 0-8, preferably 0.5-6, especially preferred 1.0 to 2.0
optionally an oxide or a number of oxides of an earth alkali metal or a number of earth alkali metals from the group magnesium, calcium, strontium and barium 0-20, preferably 0-10, especially preferred 0-5,
optionally one or more additives from the group $B_2O_3$, $MnO_2$, $Fe_2O_3$, $V_2O_5$, $TiO_2$, $Sb_2O_3$, ZnO, $SnO_2$ and fluorides 0-6, preferably 0-4
optionally one or more oxides of the rare earth metals with the atomic numbers 57, 59-64, 66-71, in particular lanthanum, yttrium, praseodymium, erbium, and europium, 0-5, preferably 0-3
wherein the total sum is 100% by weight.

"Optionally an oxide or a number of oxides" means that it is not absolutely necessary for one or more oxides to be contained in the glass melt.

In particular the body/blank contains the following components in percentage by weight:

| | |
|---|---|
| $SiO_2$ | 58.1 ± 2.0 |
| $P_2O_5$ | 5.0 ± 1.5 |
| $Al_2O_3$ | 4.0 ± 2.5 |
| $Li_2O$ | 16.5 ± 4.0 |
| $K_2O$ | 2.0 ± 0.2 |
| $ZrO_2$ | 10.0 ± 0.5 |
| $CeO_2$ | 0-3, preferably 1.5 ± 0.6 |
| $Tb_4O_7$ | 0-3, preferably 1.2 ± 0.4, |
| $Na_2O$ | 0-0.5, preferably 0.2-0.5 | wherein the total sum is 100% by weight.

In embodiment the invention is characterized in that the blank is formed from the glass melt during cooling or after cooling to room temperature, with the blank then undergoing at least a first heat treatment W1 at a temperature $T_{W1}$ over a period of time $t_{W1}$, wherein 620° C.$\leq T_{W1} \leq$800° C., in particular 650° C.$\leq T_{W1} \leq$750° C., and/or 1 minute$\leq t_{W1} \leq$200 minutes, preferably 10 minutes$\leq t_{W1} \leq$60 minutes. The form body is fabricated from the blank/heat-treated blank.

Nuclei and lithium metasilicate crystals are formed during the first heat treatment step. A corresponding lithium silicate glass ceramic blank can be formed through working into a form body, i.e., the dental object, without difficulty, wherein the tool wear is minimal.

The form body can also be fabricated through pressing from a blank or pellets of the above-described composition, wherein the one or more heat treatment steps can be carried out during the pressing procedure or after it.

In particular to obtain the final crystallization, in particular to produce lithium disilicate crystals or transform the metasilicate crystals into disilicate crystals it is provided for the lithium silicate glass ceramic blank after the first heat treatment W1 to undergo a second heat treatment W2 at a temperature $T_{W2}$ over a time $t_{W2}$, wherein 800° C.$\leq T_{W2} \leq$1040° C., preferably 800° C.$\leq T_{W2} \leq$900° C. and/or 2 minutes$\leq t_{W2} \leq$200 minutes, preferably 3 minutes$\leq t_{W2} \leq$30 minutes.

The following temperature values and heating rates are preferably chosen for the heat treatment steps leading to a pre-crystallization/final crystallization. With regard to the first heat treatment W1 it is in particular provided for a two-step approach, wherein a first holding stage is in the range 640° C. to 680° C. and a second holding stage is in the range 720° C. to 780° C. In each holding stage the heated blank is held at a temperature for a certain period of time; in the first stage this is preferably between 35 and 45 minutes and in the second stage preferably between 15 and 25 minutes.

The blank is worked through grinding or milling either after the first heat treatment stage or after the second heat treatment stage, but preferably after the second heat treatment stage to obtain the form body of the desired geometry. Subsequently, the form body is subjected to a simulated glaze firing—without actually applying a glaze—or is polished by hand. The same applies if the form body is derived through pressing.

The form body made available is then annealed in a salt melt. The salt melt may contain color-imparting additives, in particular comprising one or more lanthanides from cerium to ytterbium (atomic numbers 58 to 70) and/or one or more elements from the group vanadium, manganese, iron, yttrium, antimony.

Following removal from the salt melt, cooling and the removal of any adhering residues of salt melt/paste and if necessary to a certain degree working of the form body so made available it may be deployed particular as a dental restoration. In view of the increase in strength the form body may in particular be a multi-unit bridge.

Samples of corresponding form bodies have demonstrated that flexural strength values in excess of 800 MPa can be attained. The values were determined using the three-point method for flexural strength specified in DIN EN ISO 6872:2009-1.

The value for chemical solubility obtained in the hydrolysis test specified in DIN EN ISO 6872:2009-1 was <95 $\mu g \times cm^{-2}$. The method according to the invention therefore not only increased the strength of the form body but also its resistance to corrosion.

In particular it is provided for the salt comprising one or more alkali metal salts to be pressed/compressed into a salt body and for it to be laid on the form body or for the form body to be laid on it and the salt body then melted, so that the salt melt completely envelops the form body and the desired ion exchange can take place. The form body may be accommodated in this process in a receptacle with perforations.

According to a further proposal, to enable ion exchange to be carried out through a melted salt, which as mentioned comprises or contains one or more alkali salts, the salt is made available in aliquots in a receptacle—i.e., the second receptacle—such as a capsule with a closure that can be removed, through unscrewing or tearing off. The second receptacle can also be used at the same time as the receptacle for the form body so that the salt is melted with the form body lying on the salt. There is naturally also the possibility of firstly melting the salt and then immersing the form body in the melt. The above explanations also include the possibility of first surrounding the form body with the salt and then melting the salt. There is also the possibility of immersing the form body in the melt through a receptacle having perforations such as a wire basket.

Independently of the above, the form body should initially be at room temperature when brought in contact with the salt. In a departure from the prior state of the art the form body is not initially heated before being annealed in the salt/melt.

According to the invention it is in particular also provided for the glass phase to be 20-65% by volume, in particular 40-60% by volume.

The invention is consequently also characterized by a form body in which the lithium silicate crystals are present in the range 35-80% by volume and in particular 40-60% by volume. Lithium silicate crystals here mean the sum of lithium disilicate crystals, lithium metasilicate crystals and lithium phosphate crystals if $P_2O_5$ is contained.

The form body is in particular characterized in that the concentration of alkali metal ions that replaces the lithium ions, especially if potassium ions are used, from the surface down to a depth of 10 μm is in the range 5-20% by weight. At a depth between 8 and 12 μm from the surface the alkali ions should be present in the range 5-10% by weight. At a depth between 12 and 14 μm from the surface the alkali ions should be present in the range 4-8% by weight. At a depth of between 14 and 18 μm from the surface the corresponding range for the alkali ions is between 1 and 3% by weight. The percentage by weight of the alkali ions diminishes from layer to layer.

As mentioned, the percentage by weight values do not take into account the alkali ions already present in the form body. The numerical values hold in particular for potassium ions.

It should firstly be exemplified that as a result of the replacement of lithium ions present in the glass component of a form body of a lithium silicate glass ceramic with alkali metal ions of greater diameter the surface compressive stress is generated, leading to an increase in strength.

In the tests described below at least raw materials, such as lithium carbonate, quartz, aluminum oxide, zirconium oxide, were mixed in a drum mixer until a visually uniform mixture resulted. The compositions according to the data of the manufacturers used for the tests are given below.

The following holds in principle for the tests given below:

The mixture in question was melted at a temperature of 1500° C. for a period of 5 hours in a high-temperature resistant platinum alloy crucible. The melt was subsequently poured into molds to derive rectangular bodies (blocks). The blocks were subsequently subjected to a two-step heat treatment, designated the first heat treatment step, to create lithium metasilicate crystals as the main crystal phase (1st treatment step). The blocks were thereby heated in the first heat treatment step W1 at a heating rate of 2 K/minute to 660° C. and held at that temperature for 40 minutes. They were then heated further to 750° C. at a heating rate of 10 K/minute. The specimens were held at that temperature for 20 minutes. This heat treatment influences nucleation and lithium metasilicate crystals are formed.

The blocks were then subjected to a second heat treatment step W2 (2nd treatment step) to form lithium disilicate crystals as the main crystal phase. In this heat treatment step the blocks were maintained at a temperature $T_2$ for a period of time $t_2$. The corresponding values are given below. They were then cooled to room temperature.

Bending rods (specimens) of rectangular shape were then derived by machine from the cooled blocks (3rd treatment step) through grinding of the blocks. The bending rods had the following dimensions: length 15 mm, width 4.1 mm and height 1.2 mm. The edges of some of the specimens were then smoothed, using silicon carbide abrasive paper with a granulation of 1200. A Struers Knuth-Rotor rotary grinding machine was used for grinding. The sides of the specimens were then ground (4th treatment step). Here too, a SiC abrasive paper with a granulation of 1200 was used. A glaze firing (5th treatment step) was then carried out for some further specimens without material application. This glaze firing (designated the third heat treatment step) was carried out at a temperature $T_3$, for a period of time $t_3$. The glaze firing was carried out to seal any cracks in the surface.

The three-point flexural strength measurements were carried out as specified in DIN EN ISO 6872:2009-01. For this purpose the specimens (small rods) were mounted on two supports at a distance of 10 mm apart. A loading piston acted on the specimens between the rods, with the tip in contact with the specimen having a radius of 0.8 mm.

The specimens were also subjected to a hydrolysis test as specified in DIN EN ISO 6872:2009-01.

EXAMPLE #1

Lithium Silicate Glass Ceramic According to the Invention

The following starting composition (in percentage by weight) according to manufacturer specifications was used to derive lithium silicate glass and from that lithium silicate glass ceramic material to carry out a number of tests.

| | |
|---|---|
| $SiO_2$ | 58.1-59.1 |
| $P_2O_5$ | 5.8-5.9 |
| $Al_2O_3$ | 1.9-2.0 |
| $Li_2O$ | 18.5-18.8 |
| $K_2O$ | 1.9-2.0 |
| $ZrO_2$ | 9.5-10.5 |
| $CeO_2$ | 1.0-2.0 |
| $Tb_4O_7$ | 1.0-1.5 |
| $Na_2O$ | 0-0.2 |

The percentage of glass phase was in the range 40-60% by volume.

a) Test Series #1

Twenty rods were derived and treatment steps 1 to 5 carried out. The final crystallization (second heat treatment step) was carried out at a temperature $T_2$=830° C. for a period of time $t_2$=5 minutes. The glaze firing (5th treatment step) was carried out at a temperature $T_3$=820° C. for a period of time $t_3$=4 minutes.

Ten of these rods, without further treatment, were then subjected to a three-point flexural strength test and a mean value of 322 MPa was obtained.

The remaining ten rods were then annealed in a salt bath of technically pure $KNO_3$ at a temperature of 480° C. for 1 hour. The rods were then removed from the melt and the melt residues removed using hot water. Three-point flexural strength measurements were then carried out as described above. The mean three-point flexural strength value was 750 MPa.

b) Test Series #2

Twenty rods were derived as for test series #1. A three-point flexural strength test was carried out for 10 rods immediately after the glaze firing and a mean flexural strength value of 347 MPa was obtained. The other 10 rods were then annealed in a melt of technically pure $KNO_3$ at a temperature of 480° C. for 10 hours. The mean flexural strength value was 755 MPa.

c) Test Series #3

The chemical solubility was then determined by the method given in DIN EN ISO 6872:2009-01 for rods derived as for the first test series, both for rods annealed in a $KNO_3$ melt and rods not annealed. The rods that were not annealed in the potassium ion melt had a starting value of 96.35 µg×cm$^{-2}$. The chemical solubility value for the rods that were annealed was 90.56 µg×cm$^{-2}$.

d) Test Series #4

Rods were then derived from the aforementioned starting material, but were subjected only to treatment steps 1 to 3, i.e., the edges were not smoothed or polished and there was no glaze firing. A flexural strength measurement was performed for 10 of the 20 rods prepared and a mean value of 187 MPa obtained. The other 10 rods were then annealed in a salt melt of technically pure $KNO_3$ at a temperature of 580° C. for 10 hours. The mean three-point flexural strength value was 571 MPa.

e) Test Series #5

A further 20 rods were prepared from a lithium silicate material of the composition already described and only treatment steps 1-4 carried out for them, i.e., no glaze firing. A mean flexural strength value of 233 MPa was obtained for ten rods that were not annealed. The other 10 rods were then annealed in a $NaNO_3$ melt at 480° C. for 20 minutes. The rods had a flexural strength of 620 MPa.

The tests revealed that all specimens had an increase in strength of more than 100%, regardless of whether they received a good mechanical preparation (test series a), b), e)) or did not receive a good mechanical preparation (test series d)), before annealing in an alkali ion melt.

With regard to the deviations in the starting values, i.e., without annealing, it should be noted that the specimens were derived from different batches of starting materials of the same classification and that there were differences in the specimen preparation.

EXAMPLE #2

Lithium Silicate Glass Ceramic According to the Invention

A lithium silicate material of the following composition in percentage by weight was melted as described above:

| | |
|---|---|
| $SiO_2$ | 56.0-59.5 |
| $P_2O_5$ | 4.0-6.0 |

-continued

| | |
|---|---|
| $Al_2O_3$ | 2.5-5.5 |
| $Li_2O$ | 13.0-15.0 |
| $K_2O$ | 1.0-2.0 |
| $ZrO_2$ | 9.5-10.5 |
| $CeO_2$ | 1.0-2.0 |
| $Tb_4O_7$ | 1.0-1.2 |
| $Na_2O$ | 0.2-0.5 |

The glass phase percentage was in the range 40-60% by volume.

The melted material was poured into molds of platinum to derive round rods (pellets) for pressing in a dental furnace for pressed ceramics. A cavity of rectangular shape was thereby formed in the investment material to provide specimen rods for measurements according to Example 1. The dimensions of the rods corresponded to those for test series a) to e). The material to be pressed was pressed in the investment material at a temperature of 860° C. for 30 minutes. The rods were then removed from the investment material using aluminum oxide particles of mean diameter 110 µm with a jet pressure between 1 and 1.5 bar to keep possible damage low. The edges were then smoothed and the surfaces polished according to test series a), b) and e) (4th treatment step). There was no glaze firing (5th treatment step). Specimens were prepared accordingly and 50% of them subjected directly to flexural strength measurement as specified in DIN EN ISO 6872:2009-01. The remaining specimens were then annealed in an alkali ion melt.

f) Test Series #6

The edges of 10 specimens were smoothed and the surfaces polished. These specimens had a mean flexural strength of 264 MPa. Ten specimens were then annealed in a technically pure $KNO_3$ salt melt at 420° C. for 10 hours. The mean flexural strength was 464 MPa.

g) Test Series #7

10 specimens had a mean flexural strength of 254 MPa. 10 specimens were annealed in a technically pure $KNO_3$ salt melt at 500° C. for 10 hours. The mean flexural strength was 494 MPa.

h) Test Series #8

10 specimens that had not been annealed had a mean flexural strength of 204 MPa. A further 10 specimens were annealed in a technically pure $NaNO_3$ salt melt at 480° C. for 10 minutes. The mean flexural strength was 475 MPa.

The deviation in the starting strength values was attributable to the use of different batches and the nature of the specimen preparation.

EXAMPLE #3

Glass Ceramic of the State of the Art

Commercial pellets for pressing in a dental furnace for pressing ceramics were used. Analysis of the pellets revealed the following composition in percentage by weight:

| | |
|---|---|
| $SiO_2$ | 65.0-72.0 |
| $P_2O_5$ | 2.5-5.0 |
| $Al_2O_3$ | 1.5-3.5 |
| $Li_2O$ | 12.0-15.5 |
| $K_2O$ | 3.0-4.0 |
| $ZrO_2$ | 0-1.5 |
| $CeO_2$ | 0.5-2.3 |
| $Tb_4O_7$ | 0.5-1.0 |
| $Na_2O$ | 0-0.1 |

The glass phase percentage was 5-15% by volume.

The corresponding pellets were pressed in the dental furnace for 30 minutes at a temperature of 920° C. The edges were then smoothed and polishing carried out according to treatment step #4.

i) Test Series #9

Measurements for 10 specimens revealed a mean flexural strength of 422 MPa.

10 specimens were annealed in a technically pure $NaNO_3$ salt melt at 480° C. for 20 minutes. After annealing the mean flexural strength was 355 MPa.

EXAMPLE #4

Glass Ceramic According to the State of the Art

Commercially available blocks of lithium silicate glass ceramic of the following composition in percentage by weight according to analysis were used:

| | |
|---|---|
| $SiO_2$ | 65.0-72.0 |
| $P_2O_5$ | 2.5-5.0 |
| $Al_2O_3$ | 1.5-3.5 |
| $Li_2O$ | 12.0-15.5 |
| $K_2O$ | 3.0-4.0 |
| $ZrO_2$ | 0-1.5 |
| $CeO_2$ | 0.5-2.3 |
| $Tb_4O_7$ | 0.5-1.0 |
| $Na_2O$ | 0-0.1 |

The percentage of the glass phase was 5-15% by volume.

As for Example 1 specimen rods of corresponding dimensions were prepared according to the 3rd and 4th treatment steps through grinding of the blocks (form bodies), with their edges smoothed and subsequent polishing of the surfaces.

To yield lithium disilicate crystals as the main crystal phase in the specimens, a final crystallization according to the data of the manufacturer was carried out by heating the specimens to 850° C. for a period of 10 minutes.

j) Test Series #10

A three-point flexural strength measurement of the type described above was carried out for these 10 specimens. The mean value obtained was 352 MPa. 10 further specimens were annealed in a technically pure $KNO_3$ melt at 480° C. for 10 hours. The mean flexural strength was 594 MPa.

k) Test Series #11

A further 20 specimens were prepared from the corresponding batch and the same treatment steps carried out, including the final crystallization, but with the exception of the 4th treatment step, so that there was no good mechanical preparation of the specimens (no polishing or smoothing of the edges).

Ten of the specimens prepared in this way had a mean flexural strength value of 331 MPa. 10 specimens were annealed in a $KNO_3$ melt at 480° C. for 10 hours. The mean flexural strength value was 477 MPa.

l) Test Series #12

Specimens were prepared as for test series #10 (j). The mean flexural strength value for the 10 specimens that were not annealed was 381 MPa. 10 specimens were annealed in a technically pure $NaNO_3$ melt at 480° C. for 20 minutes. The mean strength value was 348 MPa.

A comparison of the examples/test series shows that at a low total alkali oxide content in the glass phase of the specimens, i.e., after performance of the crystallization, and with a high glass percentage in the ceramic material, lithium ions can be replaced by other alkali ions of greater diameter, so that the desired surface compressive stress is created with a consequent increase in strength. At the same time there is an improved chemical resistance. These effects are reduced or not seen at all if the percentage of the glass phase in the form body to be used, i.e., the specimen, is below 20%, in particular below 15%, as is clear from examples 3 and 4. A possible reason for this—possibly independently of the glass phase percentage—is that the alkali oxide content, i.e., the content of sodium oxide and potassium oxide, in the glass phase is more than 2.5% by weight and in particular more than 3% by weight of the starting composition. The percentage of $Li_2O$ in the starting composition is also likely to have an influence, i.e., a higher lithium ion percentage enables an increased exchange of sodium oxide and potassium oxide against lithium ions so that the compressive surface stress is increased.

A possible explanation is as follows. The ion exchange causing the surface compressive stress takes place at the interface between the surface of the glass ceramic specimens and the salt melt, wherein the process is controlled through the diffusion of alkali ions of the glass ceramic. Lithium ions diffuse from the glass ceramic to the surface where they are replaced by alkali ions from the salt melt and alkali ions from the salt melt diffuse after replacing lithium ions from the surface into the internal region of the glass ceramic. If the glass phase percentage in the lithium silicate glass ceramic is high and prior to annealing there is a relatively low percentage of potassium ions and sodium ions in the glass phase, then the motive force and thus the potential for ion exchange will be higher/more effective in comparison to glass ceramic materials in which the glass phase percentage is low and the original alkali ion percentage (sodium oxide and potassium oxide) in the glass phase is relatively high.

This may be additionally intensified by the higher lithium ion percentage in the glass phase, i.e., the lithium ion percentage that is not bound in precipitates and which is therefore available for ion exchange. The precipitates are Li—Si and Li—P precipitates.

Further measurements carried out for the lithium silicate glass ceramic specimens according to the invention have shown that the percentage of alkali ions replacing the lithium ions from the surface down to a depth of 10 μm is in the range 5 to 20% by weight. At a depth between 8 and 12 μm from the surface the alkali ions are present in the range 5-10% by weight. At a depth between 12 and 14 μm from the surface the alkali ions are present in the range 4-8% by weight. At a depth of between 14 and 18 μm from the surface the range for the alkali ions is between 1 and 3% by weight, wherein the percentage by weight of the alkali ions diminishes from layer to layer.

Irrespective of the storage of the potassium ions compared to specimens that had not been annealed in a salt melt containing potassium ions there were no differences in the microstructure upon examination using a scanning electron microscope.

It follows from the above that according to the teaching a surface compressive stress is generated when lithium ions are replaced by alkali metal ions of greater diameter. To bring about an increase in strength for form parts that are of a lithium silicate glass ceramic material, different measures according to the invention are proposed and explained with reference to the Figures.

To improve the strength of a form body 10 of a lithium silicate glass ceramic, for example in the form of a bridge or a crown, i.e., to replace lithium ions by alkali ions of greater diameter according to the teaching of the invention to generate a surface compressive stress, according to the embodiment examples of FIGS. 1 to 5, in which a container 12 (also referred to as the 6th receptacle) is used in which the bridge or crown is fully enveloped by a melt 14. To this end potassium nitrate is introduced into the receptacle 12 according to the embodiment example of FIG. 1 and melted. The temperature was approx. 480° C. The form body 10 of lithium silicate glass ceramic derived beforehand through milling with lithium disilicate crystals as the main crystal phase was introduced into the melt 14, after a glaze firing had been carried out to seal surface defects. Alternatively, smoothing by hand was carried out. The form body 10, at room temperature, was then placed in a basket 16—also referred to as the first receptacle—which was then immersed in the melt 12 with the form body 10—referred to below as the crown 10 for simplification—and annealed in the melt for a period of 8 hours. The basket 16 with the crown 10 is then removed from the melt 12 and after cooling the melt residues present were removed from the crown 10. The crown 10 was not then subsequently worked.

As can be seen from the schematic representation the melted salt is aliquoted in such a way that the crown 10 is fully immersed in the melt 14. After ion exchange has taken place the melt is disposed of so that a further restoration can be treated in a new melt.

To allow the lithium ion exchange potential to be maintained, $K_2HPO_4$ for example may be added to the potassium nitrate salt, bringing the advantage that the lithium ions leaving the lithium silicate glass ceramic body form a precipitate with the phosphate ions in the form of lithium phosphate, so that as a consequence there is no enrichment of the potassium nitrate melt with lithium ions. The $K_2HPO_4$ functions as getter for the lithium ions.

Figure 2:
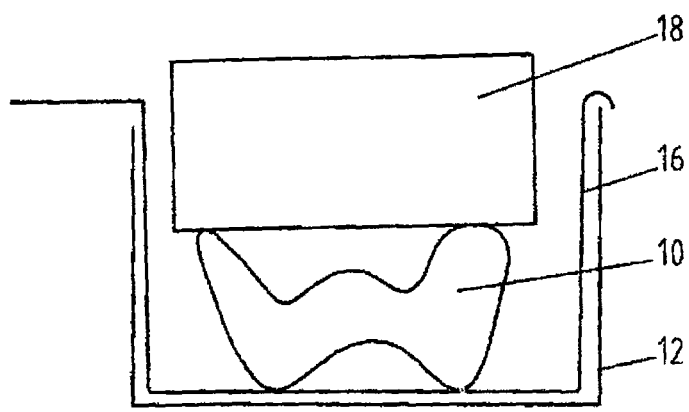
FIG. 2A schematic of a second embodiment of an arrangement to generate a surface compressive stress in a form body of a lithium silicate glass ceramic material.

In the example in FIG. 1 the crown 10 is immersed in the melt 14, whereas according to the example embodiment in FIG. 2 the crown 10 is first introduced with the basket 16 into the container 12. A pressed or compressed body 18 of an alkali metal ion salt, in particular potassium nitrate or, for example, a mixture of sodium nitrate and potassium nitrate, to just mention potassium metal ion salts as an example, is placed on the crown 10 so that through heat treatments of the aforementioned type the salt body 18 is melted so that the crown 10 is fully immersed in the melt. A temperature-time treatment can then be carried out according to the example in FIG. 1. The same applies for removal and cleaning.

Figure 3:
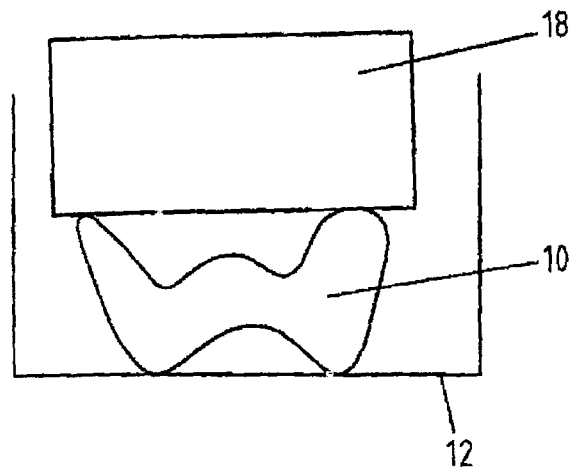
FIG. 3A schematic of a third embodiment of an arrangement to generate a surface compressive stress in a form body of a lithium silicate glass ceramic material.

The example embodiment of FIG. 3 corresponds in principle to that of FIG. 2 with the limitation that the crown 10 is introduced not by means of the basket 16, but without help into the container 12.

As in the example embodiment of FIG. 1 the form bodies of the example embodiments according to FIGS. 2 and 3 should be at room temperature at the time of contact with the salt body 18.

Figure 4:
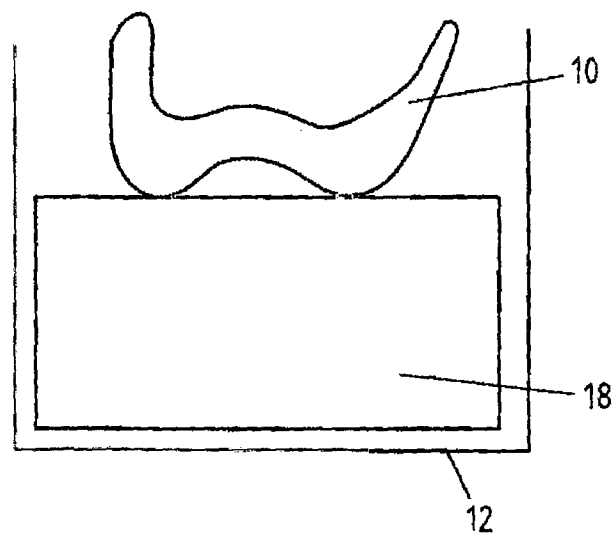
FIG. 4 A schematic of a fourth embodiment of an arrangement to generate a surface compressive stress in a form body of a lithium silicate glass ceramic material.
Figure 5:
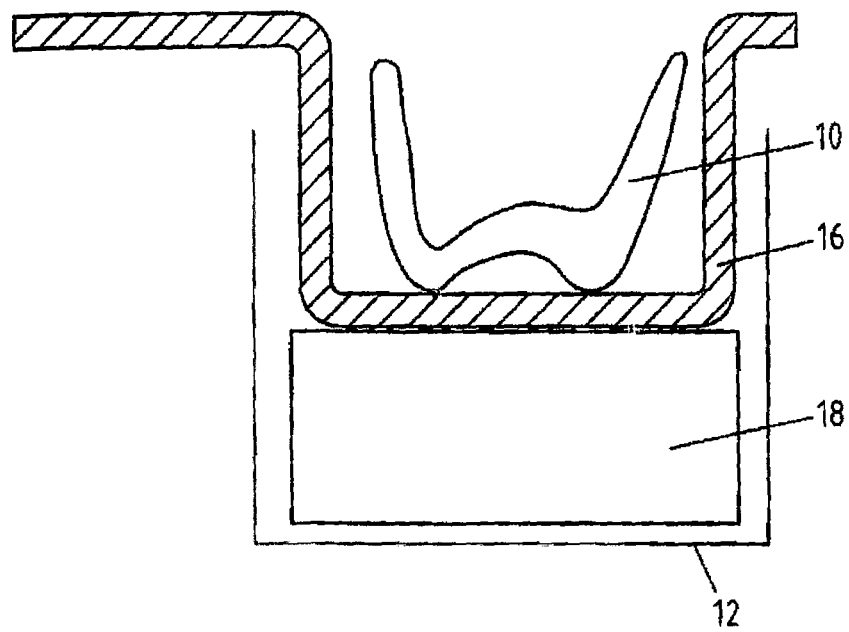
FIG. 5 A schematic of a fifth embodiment of an arrangement to generate a surface compressive stress in a form body of a lithium silicate glass ceramic material.

The example embodiments of FIGS. 4 and 5 differ from those of FIGS. 1 to 3 in that the crown 10 is placed directly on the salt body 18, or is first placed in a receptacle having perforations such as the wire basket 16, and the wire basket 16 is then placed on the salt body 18. This is in the container 12. The salt body 18 is then melted. The salt body 18 thereby has a volume that insures that the crown 10 is fully enveloped by the melt.

With respect to the salt body 18 it should be noted that this may have a plastic covering to enable simple handling without the danger of salt particles leaking out. The covering of plastic is then dissolved at the temperature deployed.

Figure 6:
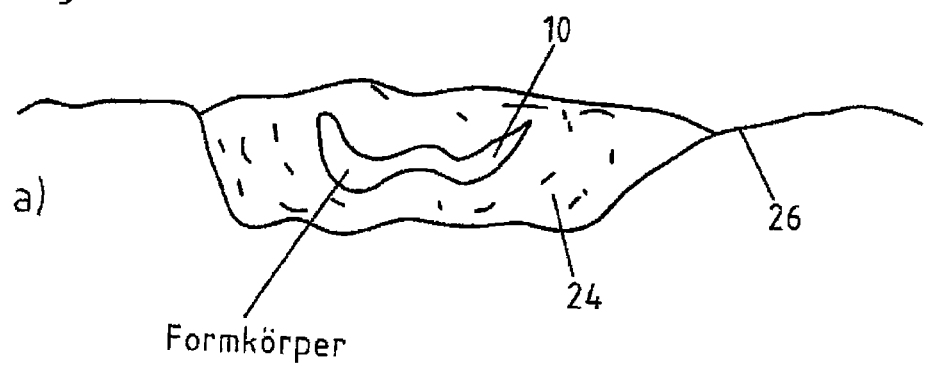
FIGS. 6a), b) Schematics of a further embodiment of an arrangement to generate a surface compressive stress in a form body of a lithium silicate glass ceramic material.
Figure 6:
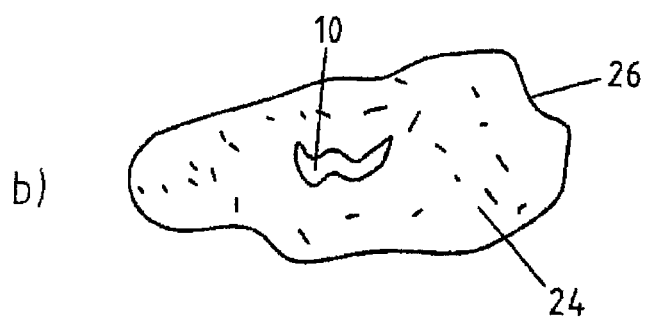

A further embodiment form is shown in FIG. 6 in which the crown 10 is fully enveloped by a melted potassium salt. To this end a heat-resistant foil, in particular a metal foil 26, is used, in which an aliquoted quantity of a potassium salt 24 is present. The foil 26 is referred to as the 4th receptacle. The quantity is chosen such that the crown 10 is fully enveloped by the salt 24/the melt formed from the salt. The metal foil 26 is then sealed, i.e., the salt 24 with the crown 10 is surrounded entirely by the metal foil 26. A temperature-time treatment is then carried out as described above to melt the salt and to anneal the crown 10 in the potassium salt melt as described above, so that ion exchange can take place and so that the surface compressive stress is generated.

Figure 7:
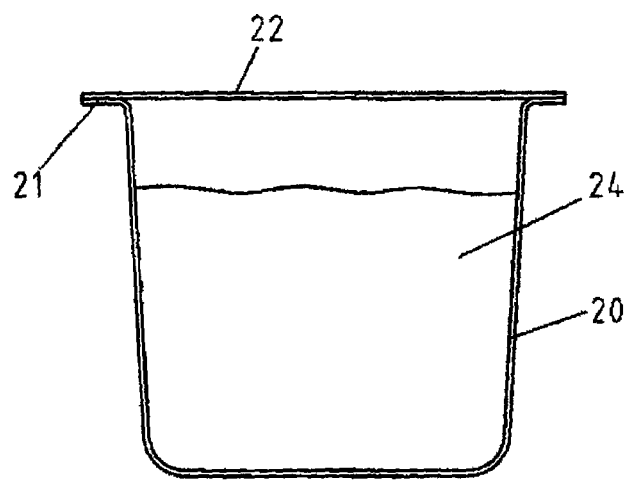
FIG. 7 A capsule to hold a salt.
Figure 8:
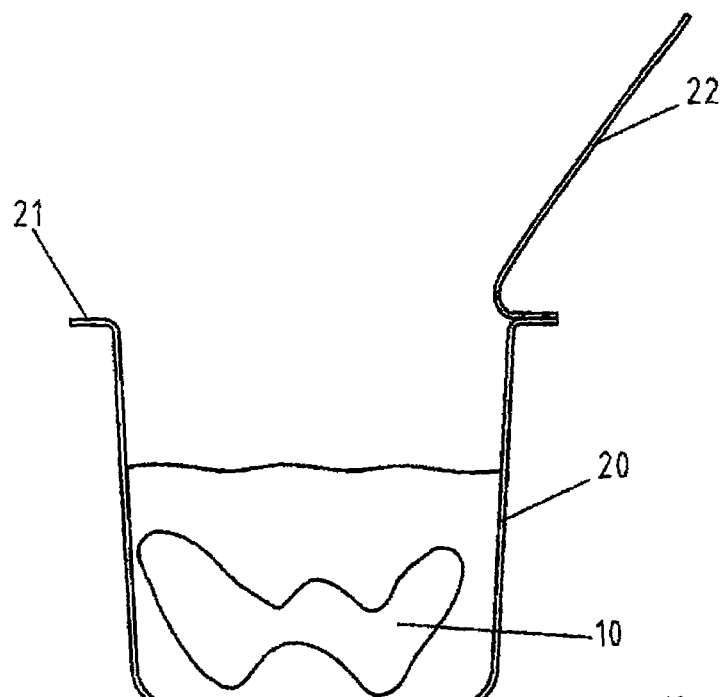
FIG. 8 The capsule according to FIG. 7 with salt melt and form body.

According to the example embodiment of FIGS. 7 and 8 an aliquoted quantity of potassium salt or a mixture of potassium salts is introduced into a capsule 20, for example one of aluminum. The capsule 20—also referred to as the second receptacle—is sealed through a lid 22 which extends along a flange-like border 21. To harden the crown 10 either the salt 24 in the capsule 20 is melted and the crown 10 then introduced or the crown 10 is placed on the salt and the crown 10 and the salt brought to the required temperature to melt the salt 24. The last option naturally involves an opened capsule 20, i.e., with the lid 22 at least partially removed from the border 21 and possibly fully removed.

It is further to be noted that there is also naturally the possibility that the crown 10 is laid in a wire basket designated as the third receptacle, so that it is immersed together with the crown 10 in the melt.

Independently thereof, the crown 10 should be at room temperature at the time of the initial contact with the salt 24/the melt.

To melt the salt in the capsule 20 designated as the second receptacle in a manner that is favorable in energy terms, a furnace 28 may be used, as shown purely schematically in FIG. 9. The furnace 28 has a receptacle 30, designated as the fifth receptacle, that is matched to the external geometry of the capsule 20 so that the capsule 20 abuts the inner wall of the receptacle 30 so that good heat transfer is possible. It can be seen from FIG. 9 that the circumferential flange-like border 21 of the capsule 20 extends in a geometrically-matched step-like indent 32 of the receptacle 30.

The above-described time/temperature treatment is not followed by further treatment steps, in particular temperature treatment steps above 200° C., to rule out the possibility of alkali metal ions, in particular sodium ions and/or potassium ions, diffusing from the surface layer of the form body such as the crown 10 into the internal region.

The invention claimed is:

1. A method to increase the strength of a form body of lithiumlithiun silicate glass ceramic, or a part thereof comprising the steps of:

preparing the form body from a glass melt which comprises at least the following as starting components: $SiO_2$, $Al_2O_3$, $Li_2O$, $K_2O$, at least one nucleating agent and at least one stabilizer, wherein the stabilizer is ZrO2 in the range of 6 to 14% by weight of the starting components;

forming a blank from the glass melt during cooling or following cooling to room temperature, said blank then being subject to at least one first heat treatment W1 at a temperature $T_{W1}$ for a time $t_{W1}$, wherein 620° C.$\leq T_{W1} \leq$800° C., and 1 minute$\leq t_{W1} \leq$200 minutes to obtain a crystallization having metasilicate crystals, disilicate crystal, or a combination of metasilicate and disilicate crystals;

providing a melt including a first salt of an alkali metal phosphate salt and a second salt of a number of alkali metals with ions of greater diameter than lithium ions, wherein the ions of greater diameter than lithium ions is selected from the group consisting of Na, K, Cs, Rb and combinations thereof ions; and wherein an aliquoted quantity of the first salt and the second salt is used for the melt;

laying the form body in a first receptacle having perforations, and then (i) immersing the first receptacle with the form body in the melt or (ii) introducing the first receptacle with the form body into the salt and the salt is then melted or (iii) laying the first receptacle with the form body on the salt or the salt body and the salt is melted at the same time as immersion of the form body in the melt that is forming;

annealing the at least a portion of the form body that is in contact with the melt for a time t at a temperature T where 620° C.≤T≤800° C. and 0.5 hours≤t≤10 hours;

replacing lithium ions of the form blank with the ions of greater diameter than lithium ions selected from the group consisting of Na, K, Cs, Rb and combinations thereof ions to generate a surface compressive stress to a depth of at least 20 microns in the form body of lithium silicate glass ceramic through the replacement of lithium ions by the number of alkali metal ions of greater diameter, wherein the replaced lithium ions from the form blank are bound to the alkali metal phosphate salt to reduce the lithium ion content in the melt by precipitating lithium phosphate; and removing the melt from the at least a portion of the form body.

2. The method according to claim 1, further comprising the step of enveloping the form body by a heat-resistant foil that includes a portioned quantity of salt and then melting the salt.

3. The method according to claim 2, wherein the portioned salt is made available in a second receptacle with a closure that can be removed.

4. The method according to claim 3, further comprising the step of melting the salt in the second receptacle and then immersing the form body in the melt.

5. The method according to claim 3, further comprising the step of immersing the form body with a third receptacle having perforations in the melt present in the second receptacle.

6. The method according to claim , further comprising the step of laying the form body on the salt before melting of the salt.

7. The method according to claim 1, wherein the melt includes one or more elements that color the form body.

8. The method according to claim 7, wherein the one or more coloring elements are one or more lanthanides with the atomic number or numbers in the range 58 to 70.

9. The method according to claim 7, wherein at least one of the one or more coloring elements is an element selected from the group consisting of vanadium, manganese, iron, yttrium, and antimony.

10. The method according to claim 7, further comprising the step of dissolving the one or more coloring elements in the melt containing alkali ions.

11. The method according to claim 1, wherein the step of annealing, the form body in is annealed in the melt, the melt including potassium ions or sodium ions, or a mixture of potassium ions and sodium ions.

12. The method according to claim 1, wherein the glass melt includes at least one coloring metal oxide.

13. The method according to claim 1, wherein the form body or a blank from which the form body is manufactured, is prepared from a glass melt that includes the following components in percentage by weight:

$SiO_2$ 50-80,
a nucleating agent 0.5-11,
$Al_2O_3$ 0-10,
$Li_2O$ 10-25,
$K_2O$ 0-13,
$Na_2O$ 0-1,
$ZrO_2$ 8-12,
$CeO_2$ 0-10,
$Tb_4O_7$ 0-8,
optionally an oxide or a number of oxides of an earth alkali metal or a number of earth alkali metals selected from the group consisting of magnesium, calcium, strontium, barium, and any combination thereof 0-20,
optionally one or more additives selected from the group consisting of $B_2O_3$, $MnO_2$, $Fe_2O_3$, $V_2O_5$, $TiO_2$, $Sb_2O_3$, ZnO, $SnO_2$, fluorides and any combination thereof 0-6,
optionally one or more oxides of the rare earth metals with the atomic numbers 57, 59-64, 66-71, 0-5.

14. The method according to claim 1, wherein the glass melt contains the following as starting components in percentage by weight $SiO_2$ 58.1±2.0
$P_2O_5$ 5.0±1.5
$Al_2O_3$ 4.0±2.5
$Li_2O$ 16.5±4.0
$K_2O$ 2.0±0.2
$ZrO_2$ 10.0±0.5
$CeO_2$ 0-3,
$Tb_4O_7$ 0-3,
$Na_2O$ 0-0.5.

15. The method according to claim 1, wherein the blank is formed from the glass melt in the course of cooling or following cooling to room temperature, said blank then being subject to at least one first heat treatment W1 at a temperature $T_{W1}$ for a time $t_{W1}$, wherein 620° C.≤$T_{W1}$≤800° C., and/or 1 minute≤$t_{W1}$≤200 minutes.

16. The method according to claim 15, wherein the first heat treatment W1 is carried out in two steps, wherein in a first step, a temperature $T_{St1}$ is set where 630° C.≤$T_{St1}$≤690° C. and/or in a second step a temperature $T_{St2}$ where 720° C.≤$T_{St2}$≤780° C. and/or the heating rate $A_{St1}$ up to the temperature $T_{St1}$ is 1.5 K/minute≤$A_{St1}$≤2.5 K/minute and/or the heating rate $A_{St2}$ up to the temperature $T_{St2}$ is 8 K/minutes≤$T_{St2}$≤12 K/minute.

17. The method according to dawn 15, wherein after the first and/or second heat treatment step, the form body is prepared from the blank through grinding and/or milling or pressing, wherein the heat treatment step or steps is/are carried out during or after pressing.

18. Use of a capsule filled with at least one alkali metal salt to create a surface stress in a form body of a lithium silicate ceramic material through the replacement of lithium ions by a number of alkali metal ions of greater diameter than the lithium ions, in that the form body is covered by a salt of alkali metal phosphate ions and the number of alkali metals ions of greater diameter than the lithium ions melted in the capsule, wherein the number of alkali metal ions of greater diameter than lithium ions is selected from the group consisting of Na, K, Cs, Rb and combinations thereof ions and wherein:

(i) the form body is prepared from a glass melt which comprises at least the following as starting components: $SiO_2$, $Al_2O_3$, $K_2O$, at least one nucleating agent and at least one stabilizer, wherein the stabilizer is ZrO2 in the range of 6 to 14% by weight of the starting components;

(ii) the blank is formed from the glass melt during cooling or following cooling to room temperature, said blank then being subject to at least one first heat treatment W1 at a temperature $T_{W1}$ for a time $t_{W1}$, wherein 620° C.$\leq T_{W1} \leq$800° C., and/or 1 minute$\leq t_{W1} \leq$200 minutes;

(iii) the lithium silicate glass ceramic blank is subjected, after the first heat treatment W1l, to a second heat treatment W2 at a temperature $T_{W2}$ for a time $t_{W2}$, wherein 800° C.$\leq T_{W2} \leq$1040° C., and/or 2 minutes$\leq t_{W2} \leq$200 minutes to obtain a crystallization having metasilicate crystals, disilicate crystal, or a combination of metasilicate and disilicate crystals; and (iv) lithium ions of the form blank are replaced with the number of alkali metal ions of greater dimeter than lithium ions is selected from the group consisting of Na, K, Cs, Rb and combinations thereof ions to generate a surface compressive stress to a depth of at least 10 microns in the form body of lithium silicate glass ceramic through the replacement of 5-20% by weight lithium ions through a depth of 10 microns by the number of alkali metal ions of greater diameter, wherein the replaced lithium ions from the form blank are bound to the alkali metal phosphate ions to reduce the lithium ion content in the melt by precipitating lithium phosphate.

* * * * *